United States Patent
Chen

(10) Patent No.: US 10,362,995 B1
(45) Date of Patent: Jul. 30, 2019

(54) OUTDOOR GROUP EXERCISE INFORMATION ADMINISTERING SYSTEM

(71) Applicant: BION INC., New Taipei (TW)

(72) Inventor: Yu-Yu Chen, Taipei (TW)

(73) Assignee: Bion Inc., New Taipei (TW)

( * ) Notice: Subject to any disclaimer, the term of this patent is extended or adjusted under 35 U.S.C. 154(b) by 0 days.

(21) Appl. No.: 15/936,809

(22) Filed: Mar. 27, 2018

(51) Int. Cl.
*A61B 5/00* (2006.01)
*A63B 24/00* (2006.01)

(52) U.S. Cl.
CPC ........ *A61B 5/7271* (2013.01); *A63B 24/0021* (2013.01); *A63B 24/0062* (2013.01); *A63B 2024/0025* (2013.01)

(58) Field of Classification Search
CPC .............. A61B 5/7271; A63B 24/0062; A63B 24/0021; A63B 2024/0025
USPC .................................................... 340/539.11
See application file for complete search history.

(56) References Cited

U.S. PATENT DOCUMENTS

| 8,001,472 B2 * | 8/2011 | Gilley .................. G06F 19/3418 715/716 |
| 9,409,052 B2 * | 8/2016 | Werner .............. A63B 24/0021 |
| 2015/0018989 A1 * | 1/2015 | Chen .................. A63B 24/0087 700/91 |
| 2015/0258372 A1 * | 9/2015 | Tagliabue ............ G01C 22/006 700/91 |
| 2016/0375306 A1 * | 12/2016 | Gu ...................... A63B 24/0021 701/430 |
| 2017/0173394 A1 * | 6/2017 | Rider .................. A63B 24/0075 |
| 2018/0147445 A1 * | 5/2018 | Peters ................ A63B 24/0062 |

* cited by examiner

*Primary Examiner* — Hirdepal Singh
(74) *Attorney, Agent, or Firm* — Rosenberg, Klein & Lee

(57) ABSTRACT

Disclosed is an exercising information administering system in an outdoor environment. A team leader and a plurality of exercising members forms an outdoor exercising group. The team leader is configured with a master controller and each of the exercising members is configured with a member controller. A communication connection device is communicated with a data transmission interface of the master controller for transmitting the outdoor exercising information to a remote data collection center for collection, administration, and analysis.

16 Claims, 6 Drawing Sheets

OUTDOOR GROUP EXERCISE INFORMATION ADMINISTERING SYSTEM

BACKGROUND OF THE INVENTION

1. Field of the Invention

The present invention relates to an exercise administering system, and in particular to a group exercise information administering system for collecting and administering exercising information of a plurality of exercising members during exercising in an outdoor environment.

2. The Related Arts

More people are becoming aware of the need to exercise in order to maintain or improve their health. Thus, a lot of exercise devices have been develop and are available. Increasing numbers of people can be found exercising outdoors (e.g., walking, running, biking).

Exercising outdoors provides a person with varied scenery and terrain. However, some people find that frequently exercising outdoors can become monotonous. Further, no any administering system or device capable of collecting and administrating exercising information is available when a number of exercising members are exercising outdoors.

SUMMARY OF THE INVENTION

Thus, an object of the present invention is to provide a group exercise information administering system for collecting and administering exercising information of a plurality of exercising members during exercising in an outdoor environment.

The present invention provides an outdoor group exercising information administering system which includes a team leader and a plurality of exercising members forming an outdoor exercising group. The team leader is configured with a master controller and each of the exercising members is configured with a member controller. A communication connection device is communicated with a data transmission interface of the master controller for transmitting the outdoor exercising information to a remote data collection center for collection, administration, and analysis.

In the above system, each of the member controllers includes a member processor; at least one outdoor exercising signal sensor connected to the member processor for sensing at least one outdoor exercising signal of the exercising member when the exercising member is doing exercising in the outdoor environment; at least one physiological signal sensor connected to the member processor for sensing at least one physiological signal of the exercising member; an identification preset unit connected to the member processor, preset with an identification code for identifying the exercising member; and a member transceiver connected to the member processor for transmitting the outdoor exercising signal, the physiological signal, and the identification code.

Optionally, each of the exercising members comprises at least one outdoor location sensor connected to the member processor of the exercising member for sensing at least one outdoor location signal of the exercising member.

In the above system, the master controller includes a leader processor; a master transceiver connected to the leader processor; a team exercising data storage connected to the leader processor for storing and organizing the outdoor exercising signal, the physiological signal, and the identification code transmitted from the member transceiver of each of the member controllers based on the identification code respectively; and a data transmission interface connected to the leader processor for transmitting the outdoor exercising signal, the physiological signal, and the identification code.

With the technical solution adopted in the present invention, the outdoor exercise information, such as outdoor exercising signals and physiological signals, transmitted from each exercising member can be further transmitted to a remote data collection center through a communication connection device for collection, administration, and analysis.

BRIEF DESCRIPTION OF THE DRAWINGS

The present invention will be apparent to those skilled in the art by reading the following description of preferred embodiments of the present invention, with reference to the attached drawings, in which.

DETAILED DESCRIPTION OF THE PREFERRED EMBODIMENTS

Figure 1:
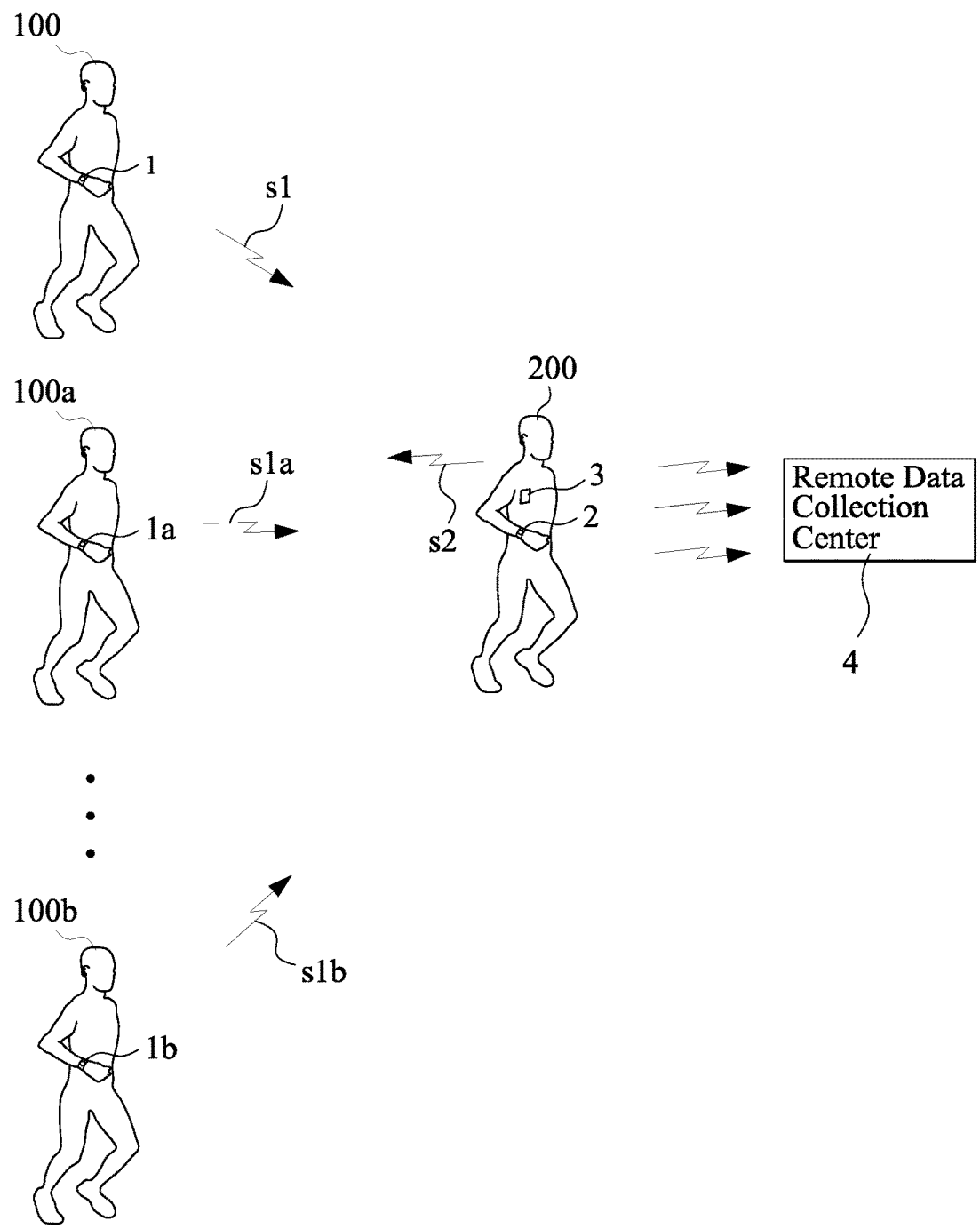
FIG. 1 is a schematic view showing an outdoor team exercising system according to the present invention.

With reference to the drawings and in particular to FIG. 1, which is a schematic view showing an outdoor team exercising system according to the present invention is composed of a plurality of exercising members 100, 100*a*, 100*b* and a team leader 200, forming an exercising group.

Figure 2:
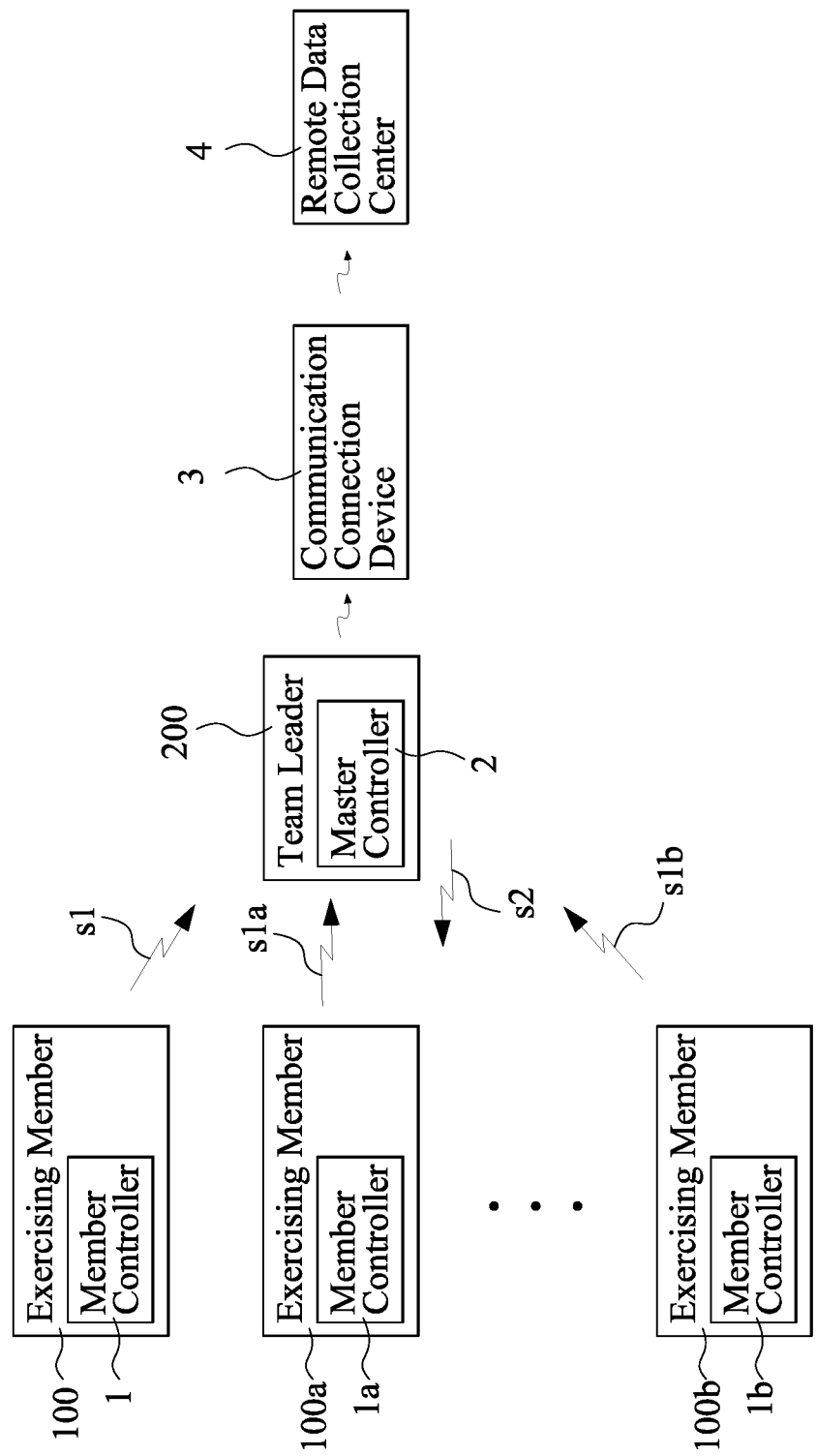
FIG. 2 is a system circuit block diagram according to a first embodiment of the present invention.

Also referring to FIG. 2, which is a system circuit block diagram according to a first embodiment of the present invention. Each of the exercising members 100, 100*a*, 100*b* is configured with a member controller 1, 1*a*, 1*b* respectively and the team leader 200 is configured with a master controller 2.

Each of the member controllers 1, 1*a*, 1*b* of the exercising members 100, 100*a*, 100*b* is capable of detecting various individual exercising signals s1, s1*a*, s1*b* and then transmitting those signals to the master controller 2 of the team leader 200.

Each of the member controllers 1, 1*a*, 1*b* may be a portable unit adapted to be worn through a conventional wearing accessory, such as a belt or a chest strip, on a selected portion of the exercising member 100 (such as wrist, chest, arm, waist, ankle, or shoe) to allow physiological signal sensors to detect various body signals of the exercising member 100. In the instant embodiment, the exercising member 100 can be a wristwatch like portable unit that is wearable on a wrist of the exercising member 100.

A communication connection device 3 is used to communicate with the master controller 2 for transmitting the exercising signals to a remote data collection center 4. The communication connection device 3 may be mounted on the team leader 200 or mounted on a crutches or a backpack carried by the team leader 200. Optionally, the communication connection device 3 and the master controller 2 may be either configured as two separated units or integrated as one unit.

Figure 3:
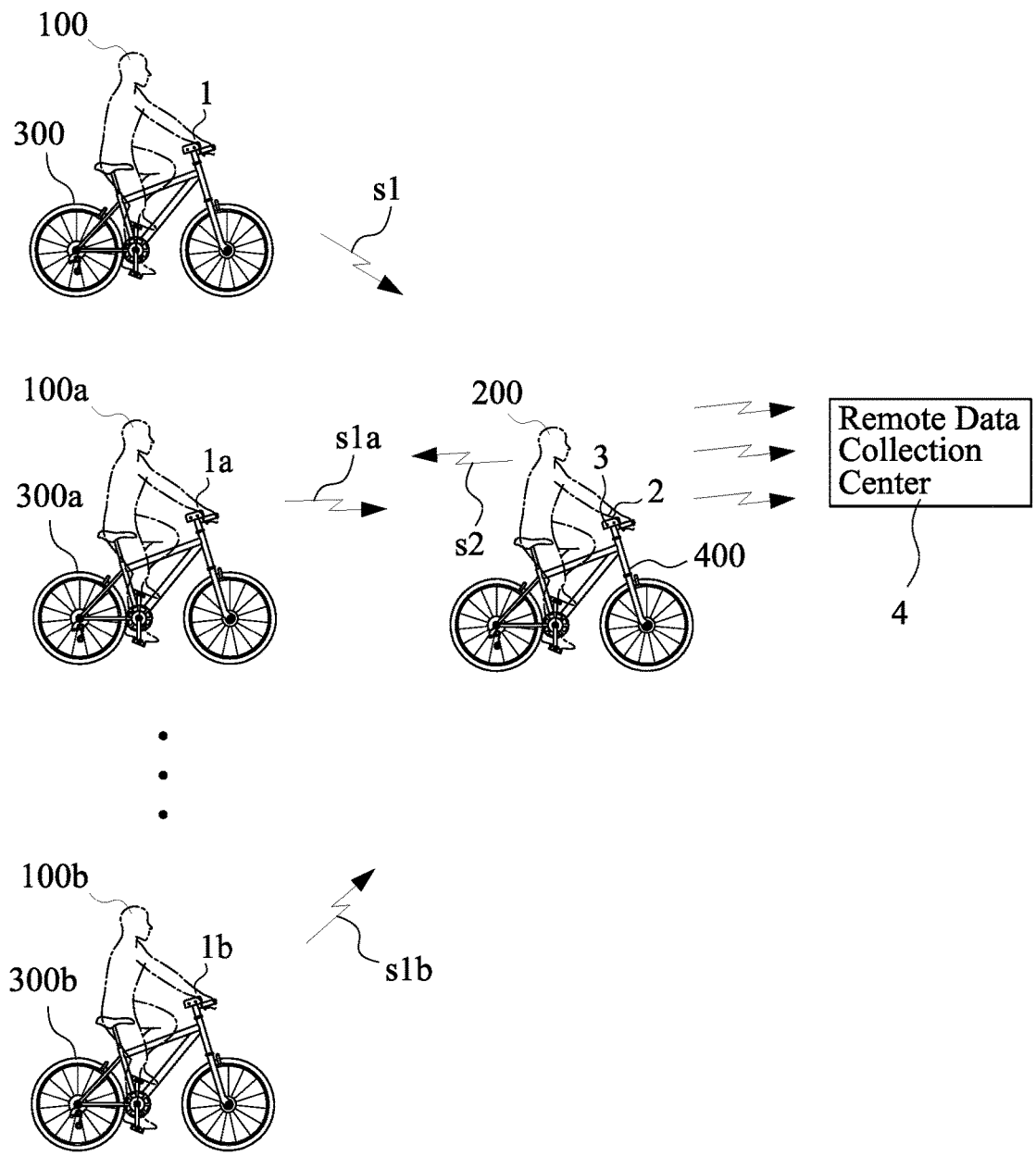
FIG. 3 is a schematic view showing an outdoor team exercising system applies to that each of the exercising members and the team leader use an exercise carriers.

FIG. 3 is a schematic view showing the outdoor team exercising system according to the present invention may apply to that the exercising members 100, 100a, 100b use exercise carriers 300, 300a, 300b respectively and the team leader 200 uses an exercise carrier 400. Each of the exercising members 100, 100a, 100b is configured with a member controller 1, 1a, 1b and the team leader 200 is configured with a master controller 2. The exercise carrier 400 may be an outdoor bicycle, skate, snowboard, surfboard, hang glider, paragliding, water activity device or aquaplane.

A communication connection device 3 is used to communicate with the master controller 2 for transmitting the exercising signals to a remote data collection center 4. The communication connection device 3 may be carried by the team leader 200 or alternatively mounted on the exercise carrier 400. The communication connection device 3 and the master controller 2 may be either configured as two separated units or integrated as one unit. Alternatively, communication connection device 3 and the master controller 2 may be incorporated in a known smart phone which is a mobile personal computer with a mobile operating system.

Figure 4:
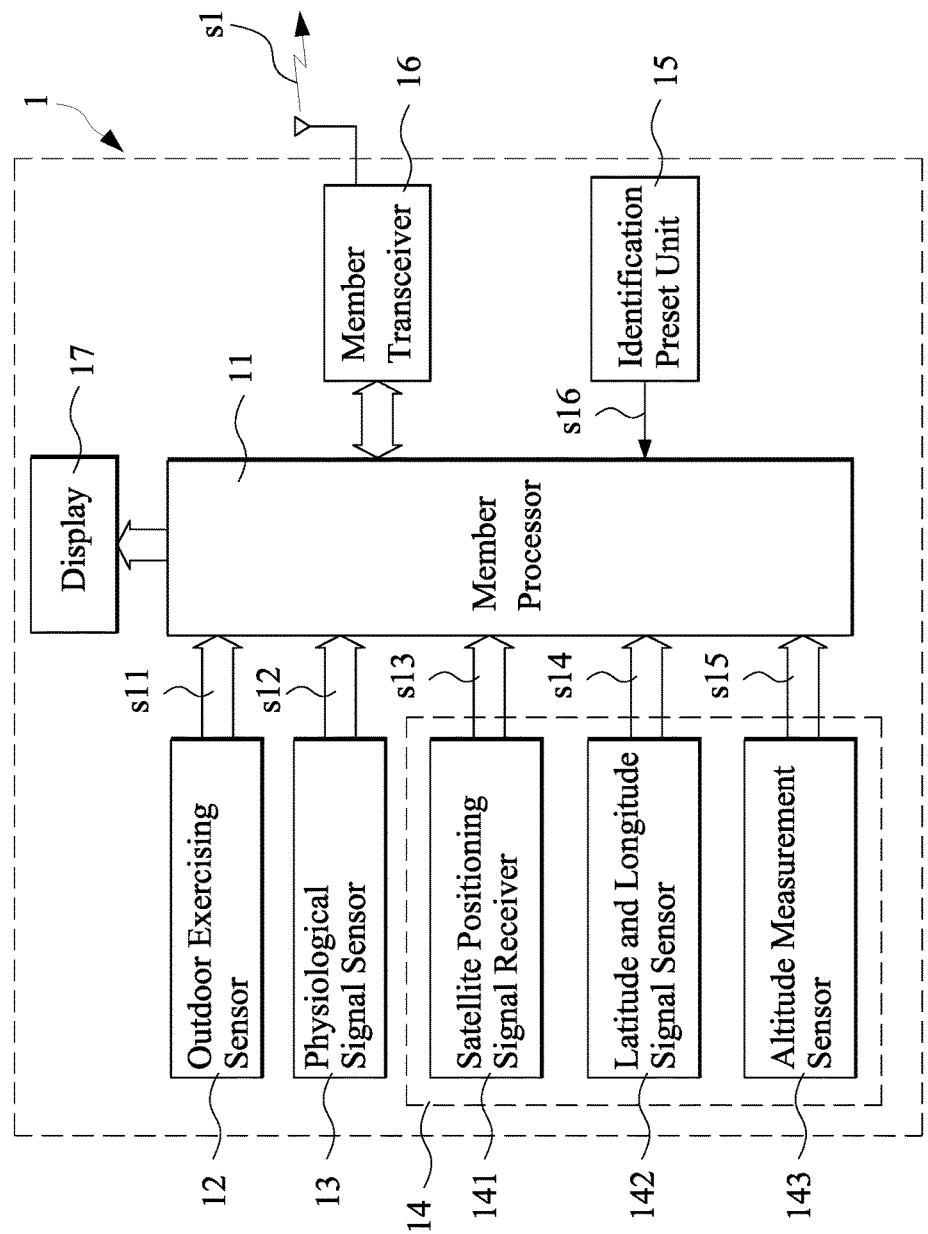
FIG. 4 is a circuit block diagram of the member controller of FIG. 2.

FIG. 4 is a functional circuit block diagram of each member controller 1 of the present invention. As shown, the member controller 1 includes a member processor 11, an outdoor exercising signal sensor 12, an identification preset unit 15, a member transceiver 16, and a display 17. Optionally, a physiological signal sensor 13 and an outdoor location sensor 14 are included in the member controller 1.

The outdoor exercising signal sensor 12 is connected to the member processor 11 for sensing at least one outdoor exercising signal s11 of the exercising member 100 during exercising. The outdoor exercising signal s11 may comprise one of pace, cadence speed, altitude, tire pressure, speed, slope, frequency and power of the exercising member 100.

The physiological signal sensor 13 is connected to the member processor 11 for sensing at least one physiological signal s12 of the exercising member 100 during exercising. The physiological signal sensor 13 is capable of detecting at least one of heart rate, blood pressure, blood glucose, body temperature, calorie of the exercising member 100.

The outdoor location sensor 14 is capable of sensing outdoor location signals of the exercising member 100. The outdoor location sensor 14 may include a satellite positioning signal receiver 141 connected to the member processor 11 for receiving at least one satellite positioning signal s13 corresponding to the location of the exercising member 100, a latitude and longitude signal sensor 142 connected to the member processor 11 for receiving at least one latitude and longitude signal s14 of the exercising member 100, and an altitude measurement sensor 143 connected to the member processor 11 for detecting at least one altitude signal s15 of the exercising member 100.

The identification preset unit 15 is connected to the member processor 11. A preset identification code s16 generated by the identification preset unit 15 is a code for identifying the exercising member 100.

The member transceiver 16 is connected to the member processor 11 for transmitting the outdoor exercising signal s11, the physiological signal s12, the satellite positioning signal s13, the latitude and longitude signals s14, the altitude signal s15, and the identification code s16.

Figure 5:
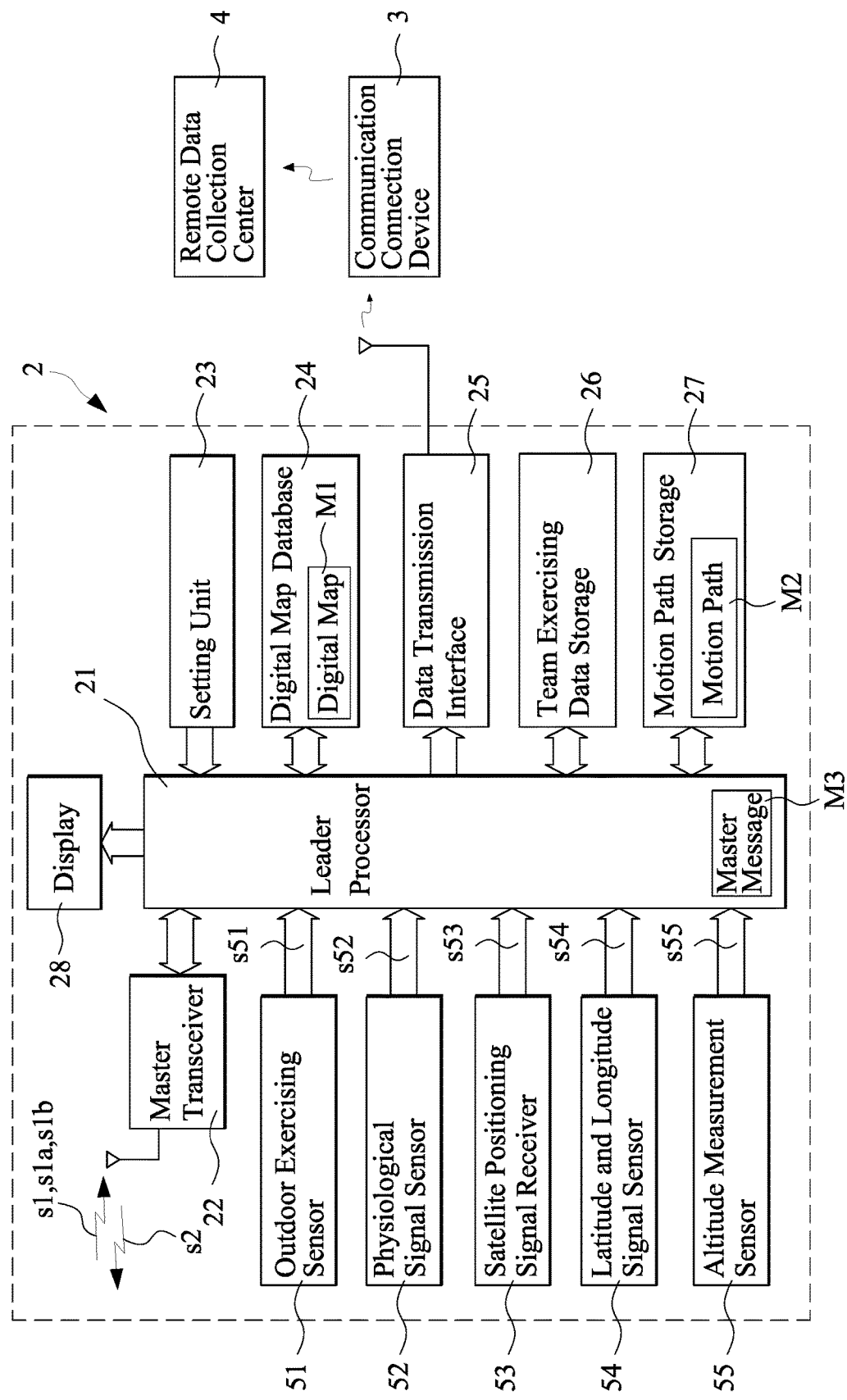
FIG. 5 is a circuit block diagram of the master controller of FIG. 2.

FIG. 5 is a functional circuit block diagram of the master controller of the present invention. As shown, the master controller 2 includes a leader processor 21, a master transceiver 22, a setting unit 23, a digital map database 24, a data transmission interface 25, a team exercising data storage 26, and a display 28.

The master transceiver 22 is used to receive the outdoor exercising signal s11, the physiological signal s12, the satellite positioning signal s13, the latitude and longitude signal s14, the altitude signal s15, and the identification code s16 transmitted from the member transceiver 16 of the member controller 1 and then send these signals to the leader processor 21.

The team exercising data storage 26 is used to store the outdoor exercising signal s11, the physiological signal s12, the satellite positioning signal s13, the latitude and longitude signal s14, and the altitude signal s15 and then organize these signals based on the identification code s16 and the setting of the setting unit 23.

The data transmission interface 25 is used to transmit the outdoor exercising signal s11, the physiological signal s12, the satellite positioning signal s13, the latitude and longitude signal s14, the altitude signal s15, the identification code s16, and the motion path M2 to the remote data collection center 4 through the communication connection device 3 in a wireless or wired manner. Optionally, the communication connection device 3 can be a mobile communication device, a tablet computer, or a personal computer.

Preferably, the data transmission interface 25 communicates with the communication connection device 3 through a NFC (Near-field communication) system that enables the data transmission interface 25 and the communication connection device 3 to establish communication by bringing them within a short distance of each other.

Similar to the member controller 1 shown in FIG. 4, the master controller 2 may be provided with an outdoor exercising signal sensor 51 for sensing at least one outdoor exercising signal s51 of the team leader 200 during exercising. Optionally, a physiological signal sensor 52 is connected to the leader processor 21 and is used to sense at least one physiological signal s52 of the team leader 200 during exercising. Optionally, the master controller 2 includes a satellite positioning signal receiver 53, a longitude signal sensor 54 and an altitude measurement sensor 55. The satellite positioning signal receiver 53 is capable of receiving at least one satellite positioning signal s53 corresponding to the location of the team leader 200. The latitude and longitude signal sensor 54 is capable of receiving at least one latitude and longitude signal s54 of the team leader 200. The altitude measurement sensor 55 is capable of detecting at least one altitude signal s55 of the team leader 200.

In a preferred embodiment of the present invention, the outdoor exercising signal s51, the physiological signal s52, the satellite positioning signal s53, the latitude and longitude signal s54, and/or the altitude signal s55 may be transmitted to the remote data collection center 4 through the data transmission interface 25 and the communication connection device 3.

Optionally, the digital map database 24 is capable of providing with at least one digital map M1 to the leader processor 21. Further, the master controller 2 includes a motion path storage 27. So, the leader processor 21 is capable of generating and storing at least one motion path M2 in the motion path storage 27 by mapping the satellite positioning signal s53, the latitude and longitude signal s54, and the altitude signal s55 with respect to the digital map M1.

Further preferably, at least one master message M3 of the master controller 2 may be transmitted to each member controller 1, 1*a*, and 1*b* through the master transceiver 22 of the master controller 2 and the member transceiver 16 of each member controller 1, 1*a*, and 1*b*. The master message M3 may be any instant messages in formatted or unformatted text to be sent from the master controller 2 to each member controller 1, 1*a*, and 1*b*. Of course, the master message M3 may include the outdoor exercising signal s51, the physiological signal s52, the satellite positioning signal s53, the latitude and longitude signal s54, and/or the altitude signal s55.

Figure 6:
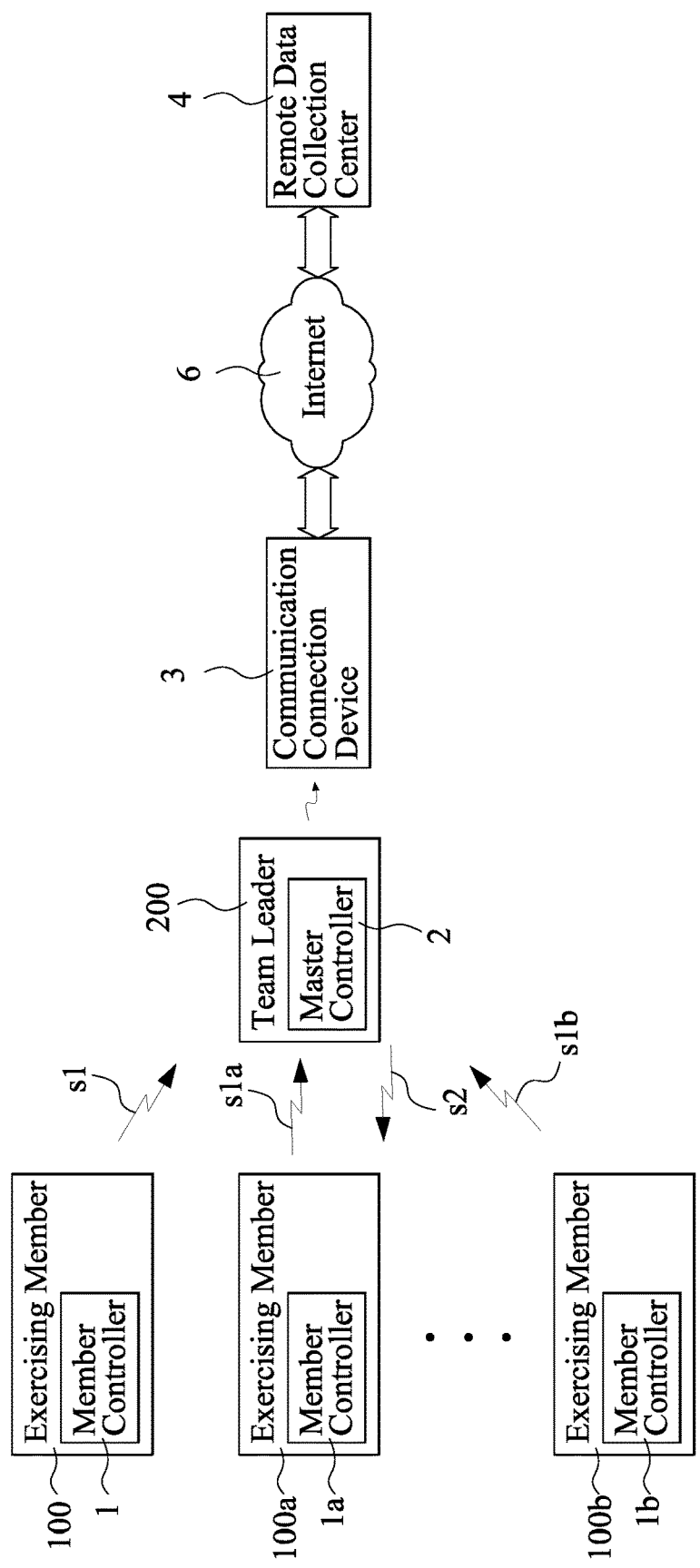
FIG. 6 is a functional system circuit block diagram according to a second embodiment of the present invention.

The remote data collection center 4 may be installed in a workstation, an Internet, a cloud, a remote database. For example, FIG. 6 is a functional system circuit block diagram according to a second embodiment of the present invention. The components of the instant embodiment are identical to those of the first embodiment and identical components are designated with the same reference numerals for consistency. In the instant embodiment, the remote data collection center 4 is installed in an Internet 6, so that the communication connection device 3 is able to transmit the individual exercising signals s1, s1*a*, s1*b* to the remote data collection center 4 through the Internet 6.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An outdoor group exercise information administering system comprising a team leader and a plurality of exercising members forming an outdoor exercising group in an outdoor environment, the team leader being configured with a master controller and each of the exercising members being configured with a member controller, wherein each of the member controllers including:
   a member processor;
   at least one outdoor exercising signal sensor connected to the member processor for sensing at least one outdoor exercising signal of the exercising member when the exercising member is doing exercising in the outdoor environment;
   an identification preset unit connected to the member processor, preset with an identification code for identifying the exercising member;
   a member transceiver connected to the member processor for transmitting the outdoor exercising signal and the identification code;
   the master controller including:
   a leader processor;
   a master transceiver connected to the leader processor and wirelessly communicated with the member transceiver of each member controller, for receiving the outdoor exercising signal and the identification code from the member transceiver of each member controller;
   a team exercising data storage connected to the leader processor for storing and organizing the outdoor exercising signal and the identification code transmitted from the member transceiver of each of the member controllers based on the identification code respectively; and
   a data transmission interface connected to the leader processor for transmitting the outdoor exercising signal and the identification code received through the master transceiver;
   a communication connection device communicated with the data transmission interface of the master controller for transmitting the outdoor exercising signal and the identification code from each exercising member to a remote data collection center;
   the exercising member including at least one outdoor location sensor connected to the member processor of the exercising member for sensing at least one outdoor location signal of the exercising member; and
   the outdoor location sensor including:
   a satellite positioning signal receiver connected to the member processor for receiving a satellite positioning signal corresponding to the location of the exercising member;
   a latitude and longitude signal sensor connected to the member processor for receiving at least one latitude and longitude signal of the exercising member; and
   an altitude measurement sensor connected to the member processor for detecting at least one altitude signal of the exercising member.

2. The outdoor group exercise information administering system as claimed in claim 1, wherein the member controller is worn on one of a selected body portion of the exercising member.

3. The outdoor group exercise information administering system as claimed in claim 1, wherein the member controller is installed on an exercise carrier selected from one of outdoor bicycle, skate, snowboard, surfboard, hang glider, paragliding, water activity device and aquaplane.

4. The outdoor group exercise information administering system as claimed in claim 1, further including at least one physiological signal sensor connected to the member processor for sensing at least one physiological signal of the exercising member.

5. The outdoor group exercise information administering system as claimed in claim 4, wherein the physiological signal including at least one of heartbeat, blood pressure, blood glucose, body temperature, calorie of the exercising member.

6. The outdoor group exercise information administering system as claimed in claim 1, wherein the outdoor exercising signal including one of pace, cadence speed, altitude, tire pressure, speed, slope, frequency and power of the exercising member.

7. The outdoor group exercise information administering system as claimed in claim 1, the master controller further including:
   at least one outdoor exercising signal sensor connected to the leader processor for sensing at least one outdoor exercising signal of the team leader when the team leader is doing exercising in the outdoor environment; and
   at least one physiological signal sensor connected to the leader processor for sensing at least one physiological signal of the team leader.

8. The outdoor group exercise information administering system as claimed in claim 1, the master controller further including a display connected to the leader processor.

9. The outdoor group exercise information administering system as claimed in claim 1, wherein the data transmission interface of the master controller communicates with the communication connection device in one of a wired and wireless manner.

10. The outdoor group exercise information administering system as claimed in claim 1, the communication connection device including one of mobile communication device, tablet computer, and personal computer.

11. The outdoor group exercise information administering system as claimed in claim 1, the remote data collection center including one of workstation, Internet, cloud, and remote database.

12. The outdoor group exercise information administering system as claimed in claim 1, wherein the communication connection device and the master controller are integrated as one unit.

13. The outdoor group exercise information administering system as claimed in claim 1, wherein the master controller and the communication connection device are incorporated in a smart phone.

14. The outdoor group exercise information administering system as claimed in claim 1, wherein the data transmission interface of the master controller communicates with the communication connection device through a NFC system.

15. The outdoor group exercise information administering system as claimed in claim 1, the master controller further including at least one master message to be transmitted to each member controller through the master transceiver.

16. An outdoor group exercise information administering system comprising a team leader and a plurality of exercising members forming an outdoor exercising group in an outdoor environment, the team leader being configured with a master controller and each of the exercising members being configured with a member controller, wherein each of the member controllers including:
   a member processor;
   at least one outdoor exercising signal sensor connected to the member processor for sensing at least one outdoor exercising signal of the exercising member when the exercising member is doing exercising in the outdoor environment;
   an identification preset unit connected to the member processor, preset with an identification code for identifying the exercising member; and
   a member transceiver connected to the member processor for transmitting the outdoor exercising signal and the identification code;
the master controller including:
   a leader processor;
   a master transceiver connected to the leader processor and wirelessly communicated with the member transceiver of each member controller, for receiving the outdoor exercising signal and the identification code from the member transceiver of each member controller;
   a team exercising data storage connected to the leader processor for storing and organizing the outdoor exercising signal and the identification code transmitted from the member transceiver of each of the member controllers based on the identification code respectively;
   a data transmission interface connected to the leader processor for transmitting the outdoor exercising signal and the identification code received through the master transceiver;
   at least one outdoor exercising signal sensor connected to the leader processor for sensing at least one outdoor exercising signal of the team leader when the team leader is doing exercising in the outdoor environment; and
   at least one physiological signal sensor connected to the leader processor for sensing at least one physiological signal of the team leader; and,
a communication connection device communicated with the data transmission interface of the master controller for transmitting the outdoor exercising signal and the identification code from each exercising member to a remote data collection center.

* * * * *